United States Patent [19]

O'Brien et al.

[11] Patent Number: 4,467,815
[45] Date of Patent: Aug. 28, 1984

[54] APPARATUS FOR MEASURING CONDITIONAL CHARACTERISTICS OF A BODY PART

[76] Inventors: William J. O'Brien, 14205 Nambe, NE., Albuquerque, N. Mex. 87123; James N. Ciraulo, 455 Live Oak Rd. NE., Albuquerque, N. Mex. 87122

[21] Appl. No.: 416,287

[22] Filed: Sep. 9, 1982

[51] Int. Cl.³ .............................................. A61B 5/10
[52] U.S. Cl. .................................................... 128/740
[58] Field of Search ....................... 128/774, 740, 744; 33/179.5 A, 179.5 E, 143 C

[56] References Cited

U.S. PATENT DOCUMENTS

| | | | |
|---|---|---|---|
| 1,296,820 | 6/1918 | Karatsu | 128/744 |
| 2,422,520 | 6/1947 | Bartley | 128/744 |
| 2,532,093 | 11/1950 | Golub et al. | 128/744 |
| 2,704,539 | 3/1955 | Fisher | 128/744 |
| 3,344,781 | 10/1967 | Allen | 128/744 |
| 3,508,540 | 4/1970 | Cavallari | 128/734 |
| 3,871,362 | 3/1975 | Dunegan | 128/736 |
| 3,933,148 | 1/1976 | Wyler et al. | 128/744 |
| 4,085,738 | 4/1978 | Kodera | 128/744 |
| 4,307,608 | 12/1981 | Useldinger et al. | 73/379 |
| 4,365,637 | 12/1982 | Johnson | 128/734 |

OTHER PUBLICATIONS

Bernard Alpers et al., "Essentials of Neurological Examination", p. 24, F. D. Davis Company.
Walker, et al., "An Apparatus to Assess Function of the Hand", 3 Journal of Hand Surgery, 189-193, (1978).
Levin, et al., "Von Frey's Method etc.", 3 Journal of Hand Surgery, 211-216, (1978).
Omer and Spinner, *Management of Peripheral Nerve Problems*, 7-15, (1980).
An, et al., "Hand Strength Measurement Instruments", 61 Arch. Phys. Med. Rehabil., 366-268, (1908).
Malinen, et al., "A New Electrical Equipment for Handgrip Testing," 11 Annals of Clinical Research, 118-120, (1979).
Whelan, "An Instrument for Use in Measuring Electrical Resistance of the Skin," 111 Science, 496-497, (1950).
Riley, et al., "Uses of the Electrical Skin Resistance Method, etc.", 137 The Johns Hopkins Medical Journal, 69-74, (1975).
Egyed, et al., "Measurement of Electrical Resistance After Nerve Injuries of the Hand," 12 The Hand, 275-281, (1980).

*Primary Examiner*—Kyle L. Howell
*Assistant Examiner*—Deidre A. Foley
*Attorney, Agent, or Firm*—Squire, Sanders & Dempsey

[57] ABSTRACT

Apparatus for measuring the sensory condition of the skin. The apparatus includes means for repeatably projecting and retracting a pair of probes and for repeatably varying the separation between the probes so that the Von Frey and Weber two point discrimination tests may be performed objectively. The apparatus also includes means for measuring skin temperature and electrical resistance with a unitary wand and for measuring the pinch and grip forces which may be applied by the fingers and hand.

8 Claims, 7 Drawing Figures

APPARATUS FOR MEASURING CONDITIONAL CHARACTERISTICS OF A BODY PART

The present application relates to apparatus for measurement of various characteristics of human body parts, such as the hand, indicative of their sensory and motor condition for diagnostic and rehabilitive purposes.

In evaluating trauma, a disease or disorder or the aftermath of medical and/or surgical treatment of a body part, such as the hand, it is helpful to measure various conditional characteristics. One of the tests of sensory condition long applied is the Von Frey pressure test in which a series of filaments of varying cross sectional area are pressed against the skin at various locations. The amount of pressure which may be applied by a filament varies with its cross sectional area and is limited by bowing of the filament. The sensitivity of a particular location is determined from the bowing pressure of the minimum size filament which can be detected by a patient. The variation in the size of the filaments, the methodology of their application and the dependence of their bowing pressures upon temperature and humidity, produce measurement results which are unreliable and, often, not reproducible. See, Levin, et al., "Von Frey's method of measuring pressure sensibility in the hand: An engineering analysis of the Weinstein-Semmes pressure aesthesiometer," 3 J. of Hand Surgery (1978), pp. 211-16.

Another test of sensory condition frequently used is the Weber two point discrimination test. In this test, two points are pressed into the skin. The distance between the points is varied between applications. The sensitivity of the nerves in the body part is measured by determining at what distance between the points the patient senses that pressure is being applied by two points, rather than by only one point. The means by which this test is usually applied are highly variable and so the results are frequently not reproducible. The practice has been to apply pressure by a variety of means such as the points of calipers and the ends of paper clips.

The Von Frey and Weber tests are described further in Omer and Spinner, *Peripheral Nerve Problems* (1980), pp. 7-15. In using both tests, the hand or other bodily part to be tested may be divided into areas and a sensibility map created by applying one or both tests to each area.

Another test of nerve condition can be obtained from measuring the temperature of the skin. An existing subjective test for determining the condition of nerves in the fingers consists of soaking the fingers in warm water and measuring the time for the resulting skin wrinkling to dissipate. Besides the subjectivity of this test, it requires a relatively long period of observation for completion.

Measurement of the electrical resistance of the skin or its inverse, conductivity, also provides useful information for evaluating sensibility and condition. See, Whelan, "An Instrument for Use in Measuring Electrical Resistance of the Skin," 111 Science (1950) pp. 496-97.

The magnitudes of compressive forces which can be exerted by the hand and fingers provide a useful index of the hand condition. Gripping forces applied by the hand and pinching forces applied by the fingers are typically measured. See, An, et. al., "Hand Strength Measurement Instruments," 61 Arch. Phys. Med. Rehabil. (1980) p. 366-68.

It is desirable to provide apparatus for measuring each of the cited indices of condition objectively, reproducibly and simply, with lightweight portable apparatus that may be taken to a patient when necessary.

SUMMARY OF THE INVENTION

The present invention provides simple apparatus by which the Von Frey and Weber tests may be conveniently, objectively and reproducibly carried out and in which skin conductivity, temperature and pinch and grip may likewise be quickly and reproducibly measured.

The Von Frey and Weber tests may be conducted by use of apparatus including a flat surface on which a finger or a portion of the hand may rest or which may be placed in contact with the skin on another portion of the body. The surface contains an elongated hole through which two probes may be projected. The separation between the probes and the amount of their projection beyond the surface is determined by repeatable mechanical adjustments made by the operator of the apparatus. Projecting the probes through the surface with the probes at their minimum separation allows measurement of a single point pressure threshold corresponding to the Von Frey test. By repeatedly increasing the separation of the probes and raising them through the surface, the Weber test two point discrimination test may be carried out. Because the separation and projection of the probes can be precisely repeated, the tests eliminate any subjective element. Results can be reproducibly carried out for various areas of the hand and other parts of the body and may even be correlated between different patients.

The other measurements are performed through the use of electrical transducers and the electrical signals produced are visually displayed in a digital format. Skin temperature is measured by applying a temperature sensitive electronic element to the skin and measuring the change of a characteristic of the element. The measured change is then visually displayed as a digital temperature value. Skin resistance is measured by applying a fixed current to the skin through two contacts. The voltage measured between the contacts is proportional to the resistance which is visually displayed in digital form in resistance units. By coordinating the temperature and conductivity measuring means, a single probe having two contacts may be used for both measurements. Pinch and grip are measured by determining the manual force needed to squeeze together two handles that are biased apart and are mechanically linked to a variable electronic element. The change in value of the variable electronic element is measured and visually displayed in digital form in units of force.

The invention is explained in detail below with reference to a preferred embodiment which is depicted in the drawings.

DETAILED DESCRIPTION OF PREFERRED EMBODIMENT

Figure 1:
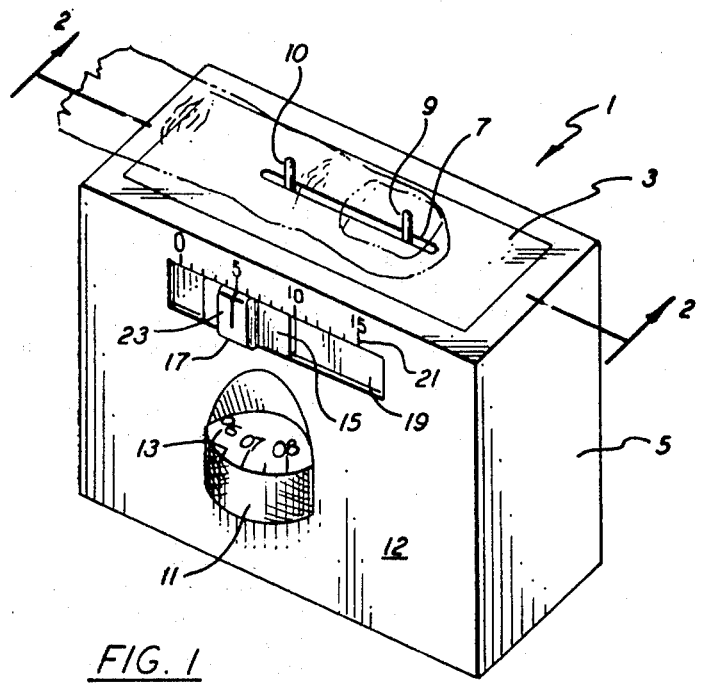
FIG. 1 is a perspective view of an embodiment of a pressure application apparatus according to the invention.

A perspective view of an embodiment of apparatus according to the invention for conducting the Von Frey and Weber tests is shown in FIG. 1. This embodiment includes a pressure application means 1 for applying pressure to the skin of a human body part, such as a finger or a hand. A finger is shown in broken lines resting on a surface 3 on the top of a generally rectangular parallelepiped housing 5. Surface 3, which is preferably transparent, contains an elongated hole 7 through which probes 9 and 10 may be projected. Probes 9 and 10 form a probe means for contacting the skin of a body part and applying pressure to it. In FIG. 1, probes 9 and 10, which preferably have radiused ends, are contacting the finger shown in broken lines. A knurled knob 11 projects from a side 12 of housing 5. The knob contains a series of reference marks 13 to indicate its relative position. Knob 11 may be rotated about an axis lying within housing 5 to raise and lower probes 9 and 10 with respect to surface 3, as further explained below. Projecting from side 12 of housing 5 is a slider 15 having a raised portion 17. Portion 17 is conveniently engaged by a thumb to move slider 15 along a slot 19 in side 12. The position of slider 15 determines the separation between probes 9 and 10, as further explained below. A scale 21 of reference numbers for determining the separation of probes 9 and 10 lies on side 12 adjacent to slot 19. A reference mark 23 on portion 17 of slider 15 aligns with the numbers of scale 21 to indicate the needle separation.

Figure 4:
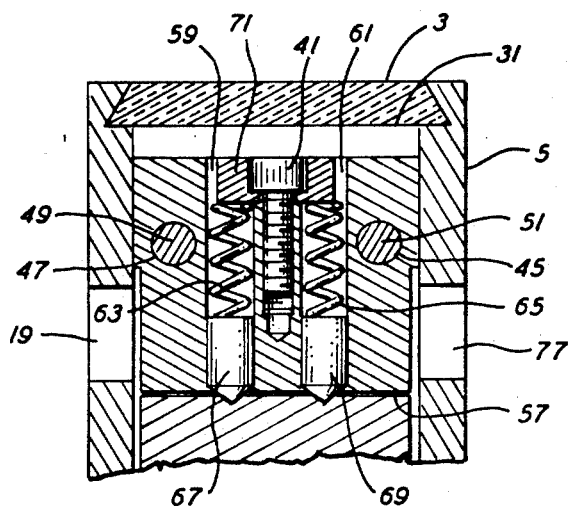
FIG. 4 is a sectional view of the embodiment of FIG. 1 taken along section line B-B of FIG. 2.
Figure 2:
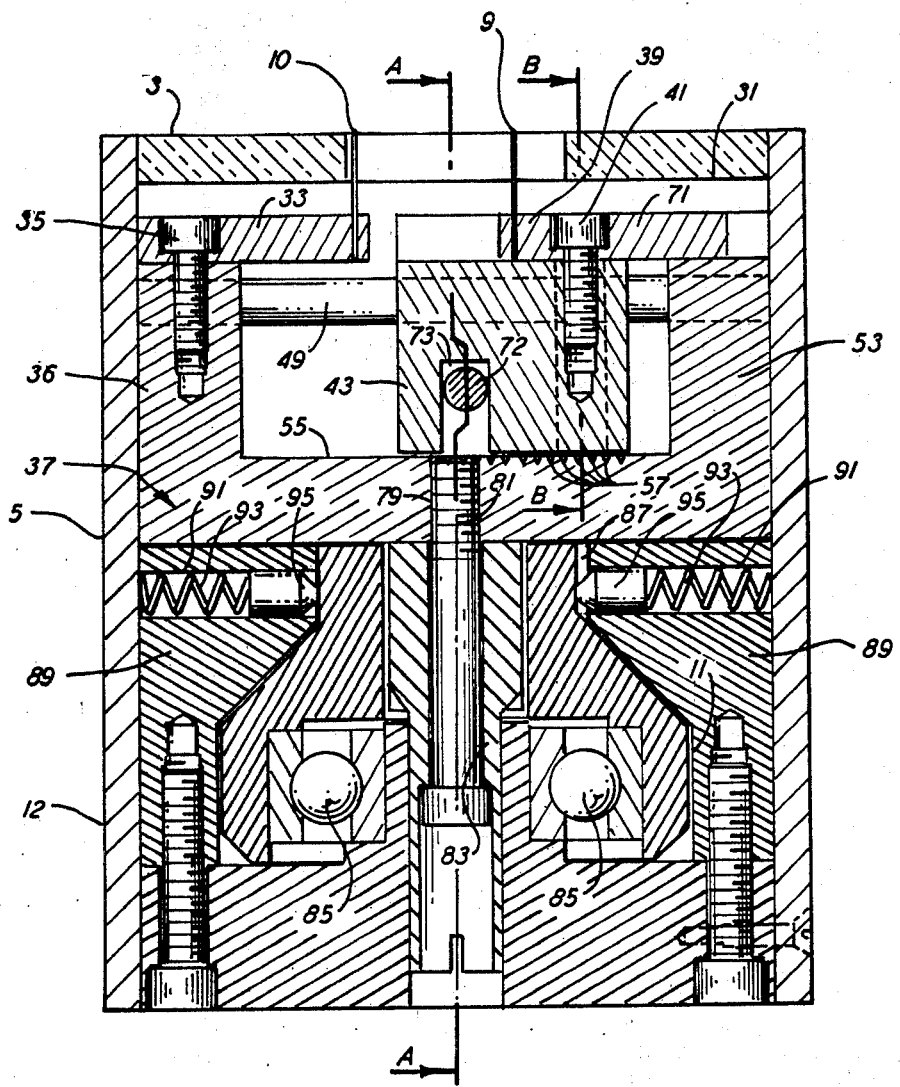
FIG. 2 is a cross sectional view of the embodiment of FIG. 1 in the direction of arrows 2-2.
Figure 3:
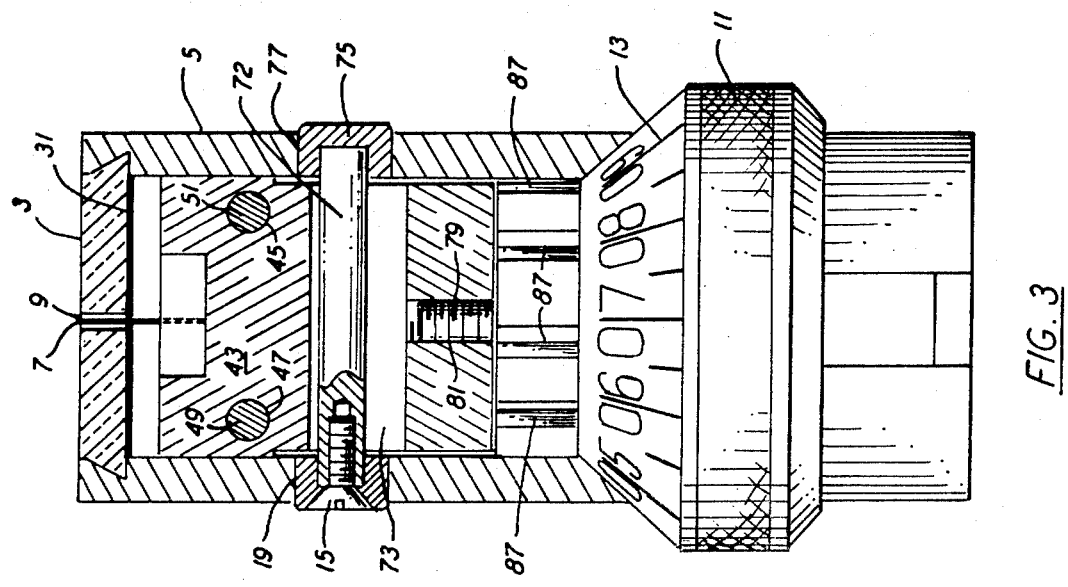
FIG. 3 is a sectional view of the embodiment of FIG. 1 taken along section line A-A of FIG. 2.

FIG. 2 depicts a sectional view of pressure application means 1 taken along a medial plane indicated by line 2—2 in FIG. 1. FIG. 3 shows a sectional view taken along the line A—A of FIG. 2 and FIG. 4 shows a sectional view taken along line B—B of FIG. 2. Taken together, FIGS. 2, 3 and 4 demonstrate the construction and operation of the embodiment. In each of the figures, like elements are given the same reference numerals. The figures show pressure application means 1 in a particular orientation, i.e., resting on a horizontal surface. The description which follows references directions with respect to that orientation with the understanding that the means may be used in any orientation.

In FIGS. 2 and 3, housing 5 is shown with its probes in their lowermost position, that is, retracted into aperture 7 so that they do not project beyond surface 3. Mounted within housing 5, generally parallel to surface 3, is a mirror 31 which contains an aperture 7, through which probes 9 and 10 may pass. By viewing the image in mirror 31, an operator of the apparatus, looking through transparent surface 3 may monitor the positions of the probes and their contact with a finger or other bodily part in contact with surface 3. Mirror 31 may be formed from a reflecting film such as aluminized Mylar. Probe 10 is mounted on a first probe support comprising a generally horizontal platform member 33 in which probe 10 is embedded. Platform member 33 is mounted by a conventional means such as a screw 35 secured to an arm 36 of a generally U-shaped cradle 37. Cradle 37 extends between and is moveably mounted by conventional means to slide up and down along the sides of housing 5. Probe 9 is embedded in a generally horizontal platform member 39 which is mounted by conventional means such as a screw 41 to a second probe support 43. Second probe support 43 contains two generally horizontal holes 45 and 47 through which pass two horizontal rods 49 and 51, respectively, which act as sliding bearings for second probe support 43. One of the ends of each of rods 49 and 51 is mounted in arm 36 of cradle 37 and the opposite ends are mounted in an opposing arm 53 of cradle 37. Second probe support 43 is mounted on rods 49 and 51 so that it may be positioned at various locations along the rods, within cradle 37 toward arm 36 or toward arm 53. Probe platform members 33 and 39 are preferably aligned or the probe lengths adjusted so that the tips of probes 9 and 10 are at the same height with respect to surface 3. When cradle 37 slides up and down within housing 5, it, with platform member 33 and 39, forms a platform by which probes 9 and 10 are slidably advanced and retracted, respectively, with respect to surface 3.

Second probe support 43 preferably extends downward, close to the inside, generally horizontal surface 55 of cradle 37. Surface 55 contains a plurality of transverse grooves 57, which are shown lying generally perpendicular to the direction of sliding of second probe support 43. As best seen in FIG. 4, second probe support 43 contains two generally vertical bores 59 and 61. Each bore contains biasing means, shown in the form of a helical spring, 63 and 65 respectively, and a pawl, 67 and 69, respectively, having a cylindrical portion and a downwardly pointed tip. A fixture 71, held in place by screw 41, blocks the top of bores 59 and 61, holding springs 63 and 65 within the bores and biasing pawls 67 and 69 downwardly toward their tips. The tips of pawls 67 and 69 may engage the one of grooves 57 when it is opposite the tips. As support 43 is slid along rods 49 and 51, pawls 67 and 69 engage and disengage from grooves 57. That is, the grooves and biased pawls comprise an embodiment of a detent means for incrementally adjusting the position of second probe support 43, with respect to the first probe support. That is, the detent means allows incremental adjustment of the separation between probes 9 and 10. A change in the separation distance is effected by movement of slider 15 of FIG. 1 which is connected to a transverse rod 72 which snugly fits inside a transverse way 73 in second probe support 43. Preferably, rod 72 extends through the full width of housing 5 and terminates in a cap 75 (shown in FIG. 3) on a side 76 of housing 5 opposite side 12. A slot 77 in side 76 similar to and opposed to slot 19, acts as a guide for cap 75. Together, cradle 37, second probe support 43 and bearing rods 49 and 51 comprise an embodiment of a displacement means for adjusting the separation of the probes. The detent means permits incremental adjustment of the separation. As will be apparent to one of skill in the art, horizontal platform member 39 is dimensioned with respect to cradle 37 to allow its horizontal travel over the desired separation range. I prefer a range of separation of 2 to 14 mm. with 1 mm. increments. That is, grooves 57 are preferably uniformly spaced on 1 mm. centers. Reference marks 21 on housing 5 correspond to grooves 57 and provide an indication of the separation of probes 9 and 10.

Cradle 37 contains a central, generally vertical bore 79 which is internally threaded. The threads are engaged by a bolt 81, shown in FIG. 2. Bolt 81 is firmly and rotatably held within a bearing 83 so that bolt 81 may be turned, causing cradle 37, i.e., the platform including members 33 and 39, to advance toward or retract from surface 3. The embodiment of bearing 83 shown includes a bearing ring 85, shown in cross section in FIG. 2, to which knob 11 (shown in FIG. 1) is rotatingly connected. Knob 11 is firmly coupled to bolt 81 to form a bolt means for advancing and retracting probes 9 and 10. Rotation of knob 11 turns bolt 81 transporting cradle 37 up or down, and thereby probes 9 and 10, toward and away from surface 3. Bearing 83 and knob 11 are conventional and therefore need no further description. Bearing 83 is mounted to housing 5 in a conventional manner, for example with screws. Platform members 33 and 39, cradle 37, bolt 79, bearing 83 and knob 11 comprise an embodiment of a probe transport means for advancing and retracting probes 9 and 10 through aperture 7.

Knob 11 contains a series of radial notches 87 above the surface bearing reference marks 13, as shown in FIGS. 1 and 3. A pair of detent retainers 89 are mounted within housing 5 adjacent knob 11, as shown in FIG. 2. Each retainer contains a generally horizontal bore 91 within which is mounted a biasing means, shown as a helical spring 93. Each spring 93 bears on housing 5 and biases a pawl 95 within bore 91 toward knob 11. Each pawl 95 has a pointed tip bearing on knob 11 for engaging one of grooves 87 when it is opposite one of pawls 95. That is, pawls 95 and notches 87 comprise an embodiment of a detent means for incrementally adjusting knob 11 and thereby incrementally adjusting the position of probes 9 and 10 with respect to surface 3. I prefer that probes 9 and 10 be mounted so as to project equally from surface 3 and be capable of retracting entirely, i.e., flush with surface 3, and of projecting a maximum of 2.0 mm. Knob 11 is conveniently calibrated in divisions of 0.05 mm. To obtain a fine adjustment capability, notches 87 may be disposed on knob 11 so that only one of them is engaged by one of the pawls at each 0.05 mm. increment.

FIGS. 2 and 3 show cradle 37 and the probes fully retracted at the beginning of a test. To carry out the Von Frey test, the probes are moved as close together as possible, 2 mm. in the preferred embodiment. The test subject places a finger on surface 3 or surface 3 is placed against some bodily part. Knob 11 is turned, raising the probes through surface 3 until the pressure sensation they generate is detected by the subject. The Weber two point discrimination test may be carried out in the same way with alternating advances and retractions of probes 9 and 10, while increasing the separation between the probes during each retraction. The steps are repeated until the test subject can detect the presence of two pressure points. The amount of the extension of probes 9 and 10 to detect pressure measures the Von Frey sensibility in an objective manner and the minimum separation of the probes for the discrimination of two pressure points measures the Weber discrimination index in a similarly objective manner.

Figure 5:
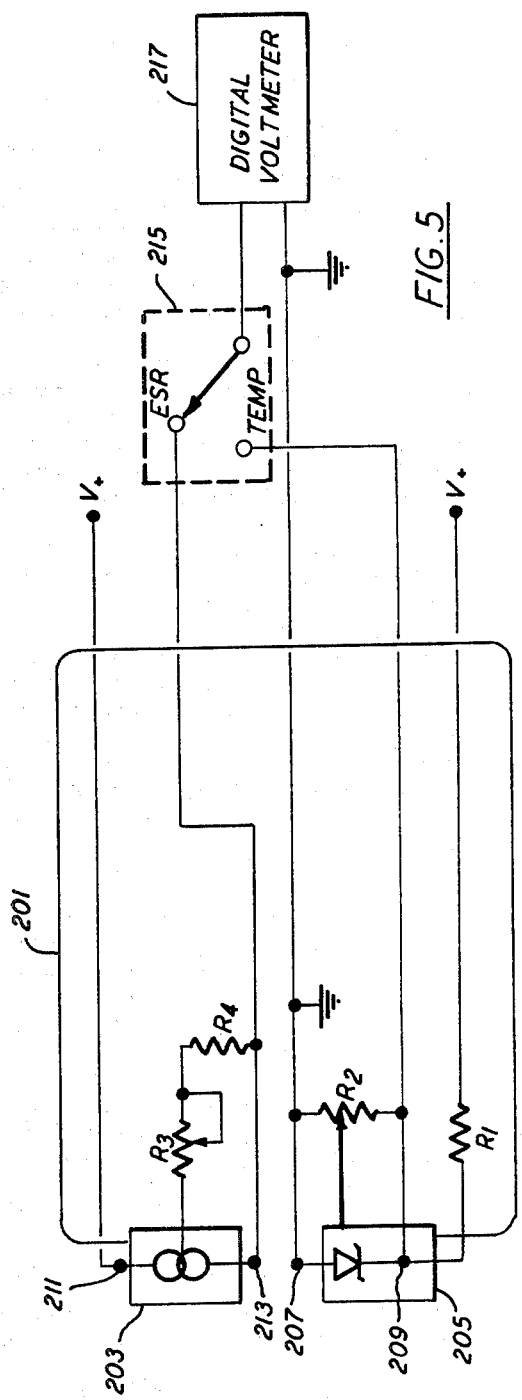
FIG. 5 is a partially schematic view of an embodiment of a conductivity and temperature measuring means according to the invention.

In FIG. 5, a partially schematic diagram of an embodiment of a means for measuring skin temperature and resistance is shown. A single wand 201 is shown greatly distorted to permit depiction of its internal details. Two circuits are shown schematically as block 203 and 205. Each block represents an encapsulated electronic circuit, each preferably including one electrical contact, which may be the circuit case, that contacts the skin to sense temperature and/or electrical resistance.

Block 205, or its case, incorporates a contact that senses the temperature of whatever it touches, such as the skin, and generates an electrical signal indicative of that temperature. A preferred embodiment of block 205 includes a temperature sensor manufactured by National Semiconductor under the designation LM335H. That circuit includes a temperature sensitive electronic element, such as the Zener diode shown. An electrical terminal 207 of block 205, which is preferably its case, is grounded. Another electrical terminal 209 of block 205 is both a power supply terminal and output terminal. Power is supplied through a resistor $R_1$ connected between a power supply designated V+ and terminal 209. A potentiometer $R_2$ is connected between terminals 207 and 209 of the preferred embodiment of block 205. Block 205 has a terminal connected to a wiping contact of potentiometer $R_2$ for calibrating the circuit within it. The voltage across terminals 207 and 209 varies, preferably linearly, with the temperature of block 205. Therefore, a measurement of that voltage is a direct measurement of the temperature of the object, such as the skin, which block 205 touches.

Block 203 indicates another circuit, the case of which preferably acts as another contact on probe 201. The case of block 203 is one terminal of a constant current source for causing a current to flow across whatever object is in contact with blocks 203 and 205. Block 203 may be commercially available integrated circuit such as the circuit designated LM334H and manufactured by National Semiconductor. The case of block 205, i.e., terminal 207, is preferably grounded so that a current path is established between the cases of blocks 203 and 205. Power is supplied from a power supply designated V+ to an electrical terminal 211 of block 203. The voltage produced by the current flowing between blocks 203 and 205 is measured across an output terminal 213 of block 203 and grounded terminal 207 of block 205. The preferred embodiment of block 203 includes a calibrating terminal 213 to which series-connected variable and fixed resistors, $R_3$ and $R_4$, are connected. $R_4$ is connected to terminal 213 of block 203. When block 203 is the preferred constant current source, the same current is caused to flow between the contacts regardless of the resistance between them. As a consequence, the voltage produced between the contacts by the current is a direct measure of the resistance between the contacts.

A two pole switch 215 allows connection of either terminal 213, i.e., terminal ESR of switch 215, for measuring skin resistance, or terminal 209, i.e., terminal TEMP of switch 215, for measuring skin temperature, to a digital voltmeter 217. Voltmeter 217 provides a visual display in digital format of the voltage at the selected terminal of switch 215. If the temperature/voltage characteristic of block 205 is linear, as preferred, the voltage at terminal TEMP, corresponding to skin temperature, may be converted by conventional passive scaling techniques to provide a direct digital display on voltmeter 217 of temperature in degrees. Likewise, if the current source in block 203 causes a fixed current to flow between blocks 203 and 205, the voltage at terminal ESR, corresponding to skin resistance, is directly proportional to the resistance of the skin. By scaling the displayed voltage in a conventional, passive manner, voltmeter 217 can directly display skin resistance in ohms. Selectable digital display ranges of from 1000 to 100,000 ohms and from 100,000 to 1,000,000 ohms for measuring skin resistance are preferred. Voltmeter 217 therefore acts as an indicating means, which along with the described wand construction that forms a sensing means, form a measuring means for measuring skin temperature and resistance.

Unitary wand 201 provides a means for sensing both skin temperature and resistance quickly and, through switch 215, almost simultaneously. Maps of temperature and resistance over various areas of the skin can easily be prepared through a series of rapid measurements with the single wand.

Figure 6:
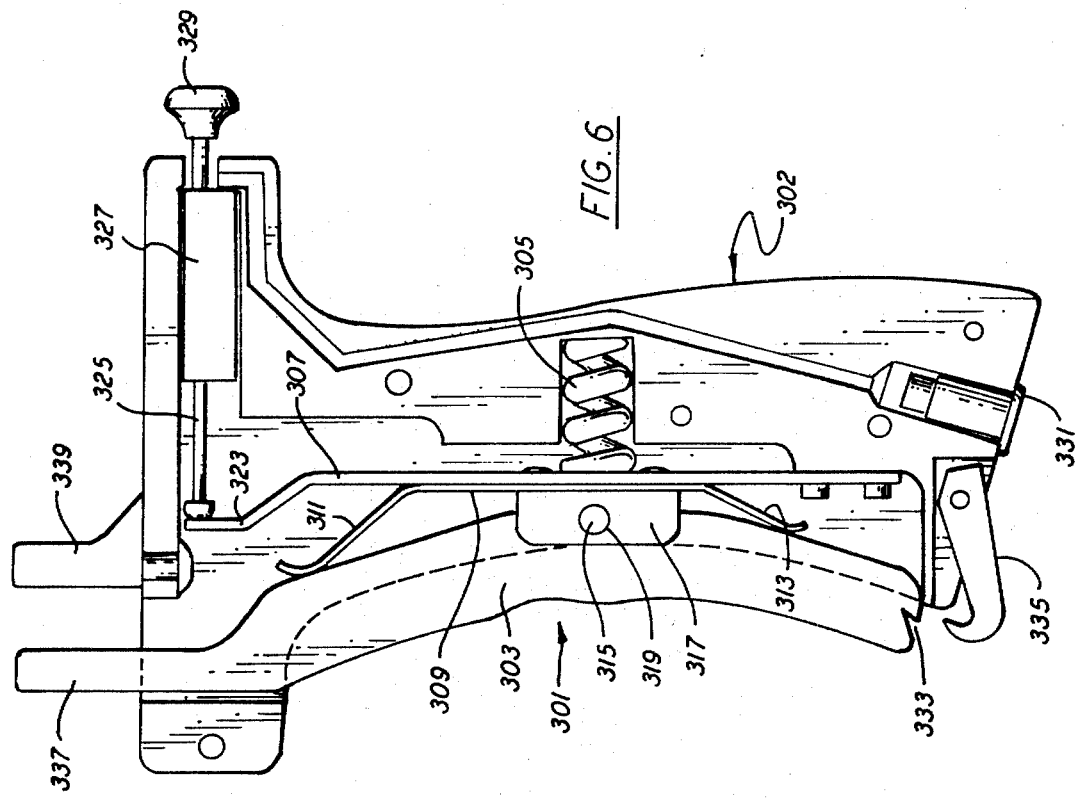
FIG. 6 is a sectional view of an embodiment of a force sensing means according to the invention.

In FIG. 6 a sectional view of an embodiment of a force sensing means for measuring the gripping and pinching forces which may be exerted by hand and the fingers, respectively, is shown. The apparatus of FIG. 6 includes a pistol grip 301. The pistol grip includes a stationary part 302 and a moveable part 303 positioned along one of the gripping surfaces of the pistol grip. Moveable part 303 is moveable relative to stationary part 302. The moveable part is biased outwardly from the stationary part of the grip by biasing means shown as a helical spring 305 mounted on stationary part 302 and pushing on moveable part 303. Spring 305 bears on one side of the medial portion of a lever 307. Lever 307 is firmly attached at one end to the base of stationary part 302 of grip 301 and has an unattached opposing end. A blade spring 309 is attached to the medial portion of lever 307 opposite spring 305. Extended arms 311 and 313 on blade spring 309 bear on the moveable part 303 of grip 301 to resist rocking of the moveable part when a gripping force is applied to it. A pivot comprising a pin 315 and a bearing 317 complete the mechanical linkage of stationary and moveable parts 302 and 303 with lever 307. Bearing 317 is mounted on the medial portion of blade spring 311, preferably by screws which pass through lever 307 and blade spring 311 to engage bearing 317. Bearing 317 contains a hole 319 through which pin 315 passes. Pin 315 is firmly attached to moveable part 303.

An unattached end 323 of lever 307 bears on one end of a sliding rod 325 which passes through a potentiometer 327, preferably having a linear resistance characteristic, and controls the position of its wiping contact. Potentiometer 327 is a variable resistance means. The opposite end of rod 325 is fitted with a knob 329 which protrudes from the pistol grip. The electrical leads from potentiometer 327 are passed through the grip to an electrical connector 331 located in the base of grip 301. Also located at the base end of the grip on moveable part 303 is a notch 333 which a pivoted hook 335 on stationary part 303 may engage. The engagement of notch 333 and hole 335 locks one end of moveable part 303 for measurement of pinch forces as explained below.

Two protrusions 337 and 339 extend from the side of the pistol grip opposite its base. Protrusion 337 is an extension of moveable part 303. Protrusion 339 is firmly attached to stationary part 302 of grip 301 and is stationary with respect to it. Protrusions 337 and 339 are formed for easy grasping by fingers.

As one skilled in the art will appreciate, the grip mechanism is preferably contained within a pistol grip housing which may be made of moldable material, such as metal or plastic, and preferably has two halves so that the grip can be assembled and disassembled in a conventional manner for access to the internal, working parts of the invention.

In operation, dynamic hand gripping forces are measured by applying a grip to the unit with the hand and squeezing moveable part 303 and stationary part 302 together against the resistance of spring 305. Displacement of moveable part 303 displaces the free arm 323 of lever 307, which forms a linkage between moveable portion 303 and the wiping contact of potentiometer 327, displacing rod 325. As a result, the position of the wiping contact of potentiometer 327 changes so that the resistance between the wiping contact terminal and another terminal of the potentiometer changes. The maximum dynamic gripping force, i.e., the maximum displacement of rod 325, is sensed by measuring the resistance change. Once displaced, rod 325 does not return to its initial position automatically so that the maximum displacement and force may be measured. The presence of bearing 317 allows moveable part 303 to tilt or pivot, subject to the stabilizing forces of blade spring 309, on pin 315. This degree of freedom permits compression of spring 305 without any leverage forces of significance acting to compress the spring.

In a similar fashion the pinching force, i.e., the force exerted between thumb and forefinger, is measured by the compression of protrusions 337 and 339. To sense pinch forces, moveable portion 303 is first locked at its base by latching hook 335 in notch 333. The locking provides a fulcrum for moveable part 303 which acts as a lever for measuring pinch force. The displacement of protrusion 337, because it is an extension of lever 307, displaces rod 325, as explained before, changing the position of the wiping contact of potentiometer 327. Measurement of the resulting resistance change is a direct measurement of the maximum, dynamic pinch force exerted.

Regardless of the type of force measured, potentiometer 327 is reset to its initial position by pressing knob 329 so that rod 325 is pushed to its initial position in contact with lever 307, when no pinch nor grip force is being applied. Potentiometer 327 is a commercially available device, such as the model LCP8-10-50K sold by ETI of Oceanside, Calif.

Figure 7:
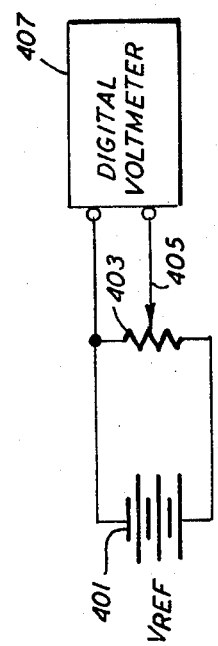
FIG. 7 is a schematic diagram of an embodiment of a force sensing means according to the invention.

A resistance sensing means for sensing changes in resistance, and thereby measuring the pinch or grip force exerted on grip 301, is shown schematically in FIG. 7. A reference voltage source 401 places a stable voltage across potentiometer 403, which corresponds to potentiometer 327 of FIG. 7. The voltage between the one terminal of potentiometer 403 and its wiping contact terminal 405 is measured by a digital voltmeter 407 which includes a digital display means for displaying the voltage measured in digital format. Initially, wiping contact 405 is in direct electrical contact with the terminal of potentiometer 403 connected to voltmeter 407, so that the measured voltage is zero. When wiping contact 405 is displaced by a grip or pinch force, if potentiometer 403 has the preferred linear resistance characteristic, a voltage equal to some fraction of the reference voltage corresponding to the amount of spring displacement, is measured by voltmeter 407. If the biasing means, as well as potentiometer 403, has a linear characteristic, then the amount of displacement, i.e., the amount of the resistance change, and the amount of the voltage change, is direct measure of the maximum force exerted. By conventional scaling techniques, the voltage visually displayed by voltmeter 407 may be displayed in units of force. Together, the force sensing means of FIG. 7 and resistance sensing means of FIG. 8 form a force measuring means for measuring pinch and grip forces and displaying these values in a visual, digital format.

It is preferred that a single digital voltmeter be used to display skin temperature, skin resistance and pinch and grip forces. By adding additional poles to the switch 215 of FIG. 6, the signals indicating force may be displayed on the same voltmeter as used for skin resistance and temperature measurements. Each switch position may include conventional scaling means so that a direct display in the desired units (e.g., °C., ohms, kg) is obtained. It is preferred that the apparatus, i.e., the temperature and resistance sensing means and the indicating means, all be battery powered so that the apparatus is compact and portable for ready use wherever a patient is located.

The invention has been described with respect to a preferred embodiment. Those skilled in the art will recognize various additions, substitutions and modifications within the spirit of the invention. Therefore, the scope of the invention is limited solely by the following claims.

We claim:

1. Apparatus for measuring the sensory condition of the skin, said apparatus comprising:
    a housing including a surface for contacting the skin, said surface including an aperture,
    two needlelike probes having radiused ends simultaneously projectable through said aperture for contacting and applying pressure to the skin,
    platform means disposed within said housing, carrying said probes and including a threaded hole, for advancing and retracting said probes simultaneously relative to said surface, said probe means including probe displacement means for adjusting the separation between probes and,
    bolt means rotatably mounted to said housing and engaging said threaded hole for advancing and retracting said platform means in response to rotation of said bolt means.

2. The apparatus of claim 1 wherein said bolt means comprises first detent means for incrementally advancing and retracting said platform means.

3. The apparatus of claim 2 wherein said bolt means comprises a bolt and a knob mounted on said bolt, and said first detent means comprises a plurality of radial notches in said knob and a pawl mounted to said housing and biased to engage a said notch opposed to said pawl.

4. The apparatus of claim 1, said platform means including first and second probe supports, wherein one of said probes is mounted on each of said first and second probe supports, and said second probe support is slidably mounted relative to said first probe support to adjust the separation between said probes.

5. The apparatus of claim 4 wherein said probe displacement means further comprises second detent means for incrementally adjusting the separation between said probes.

6. The apparatus of claim 5 wherein said second detent means further comprises a plurality of grooves in one of said probe supports disposed transversely to the direction of sliding of said second probe support relative to said first probe support, and a pawl mounted on the other of said probe supports and biased to engage a said groove opposed to said pawl.

7. The apparatus of claim 1 wherein said surface is transparent and said housing includes a mirror visible through said surface for observing said probe means.

8. The apparatus of claim 4 wherein said first probe support comprises a cradle having a base from which extend two opposing legs, at least one rod joined to each of said opposing legs and said second probe support is slidably mounted on said rod.

* * * * *